United States Patent
Gunji et al.

(10) Patent No.: US 7,999,565 B2
(45) Date of Patent: Aug. 16, 2011

(54) INSPECTION APPARATUS AND INSPECTION METHOD USING ELECTRON BEAM

(75) Inventors: Yasuhiro Gunji, Hitachiota (JP); Hiroshi Miyai, Hitachi (JP); Shigeya Tanaka, Hitachi (JP)

(73) Assignee: Hitachi High-Technologies Corporation, Tokyo (JP)

( * ) Notice: Subject to any disclaimer, the term of this patent is extended or adjusted under 35 U.S.C. 154(b) by 278 days.

(21) Appl. No.: 12/348,586

(22) Filed: Jan. 5, 2009

(65) Prior Publication Data

US 2009/0123059 A1 May 14, 2009

Related U.S. Application Data

(62) Division of application No. 11/379,463, filed on Apr. 20, 2006, now Pat. No. 7,518,383.

(30) Foreign Application Priority Data

Apr. 25, 2005 (JP) ................................ 2005-125859

(51) Int. Cl.
*G01R 31/305* (2006.01)
(52) U.S. Cl. ................................................. 324/754.22
(58) Field of Classification Search .......... 324/750–752, 324/765, 158.1, 761–762; 250/206, 207, 250/310, 311; 382/147
See application file for complete search history.

(56) References Cited

U.S. PATENT DOCUMENTS

| | | | |
|---|---|---|---|
| 5,717,207 A | 2/1998 | Koguchi et al. | |
| 6,797,975 B2 | 9/2004 | Nishiyama et al. | |
| 7,034,298 B2 * | 4/2006 | Miyai et al. | 250/310 |

FOREIGN PATENT DOCUMENTS

| | | |
|---|---|---|
| JP | 2-142045 A | 5/1990 |
| JP | 6-139985 A | 5/1994 |
| JP | 09-045271 | 2/1997 |
| JP | 2000-105824 | 4/2000 |
| JP | 2003-83917 A | 3/2003 |
| JP | 2003-098111 | 4/2003 |
| JP | 2003-218181 | 7/2003 |
| JP | 2004-239728 | 8/2004 |
| JP | 2005-061837 | 3/2005 |

OTHER PUBLICATIONS

Japanese Office Action, issued in Japanese Patent Application No. 2005-125859, dated Jul. 9, 2010.

(Continued)

*Primary Examiner* — Huy Phan
*Assistant Examiner* — Tung X Nguyen
(74) *Attorney, Agent, or Firm* — McDermott Will & Emery LLP

(57) ABSTRACT

A visual inspection apparatus and method using the scanning electron microscope are disclosed. An electron beam is scanned repeatedly on a sample, and an inspection and a reference image are generated by the secondary electrons generated from the sample or reflected electrons. From the differential image between the inspection image and the reference image, a defect is determined. The number of pixels in the generated image along the direction of repetitive scanning by the electron beam can be changed.

6 Claims, 6 Drawing Sheets

OTHER PUBLICATIONS

Japanese Office Action, w/ partial English translation thereof, issued in Japanese Patent Application No. JP 2005-125859 dated Nov. 4, 2009.

T. Shimaya, "260 Million Pixels Ultra Fine Digital Scanning Microscope Imaging System (*Practical Commercialization of Ultra High-Definition Digital SEM Image*)," The Cell, vol. 32, No. 10, Sep. 20, 2000, pp. 30-33; w/ partial English translation thereof.

Japanese Office Action, w/ partial English translation thereof, issued in Japanese Patent Application No. JP 2005-125859 dated Mar. 9, 2010.

"Electron Ion Beam Handbook," ed. 132 Committee of Japan Society for the Promotion of Science, 1986, pp. 622-623, Nikkan Kogyo Shimbun, Ltd.

* cited by examiner

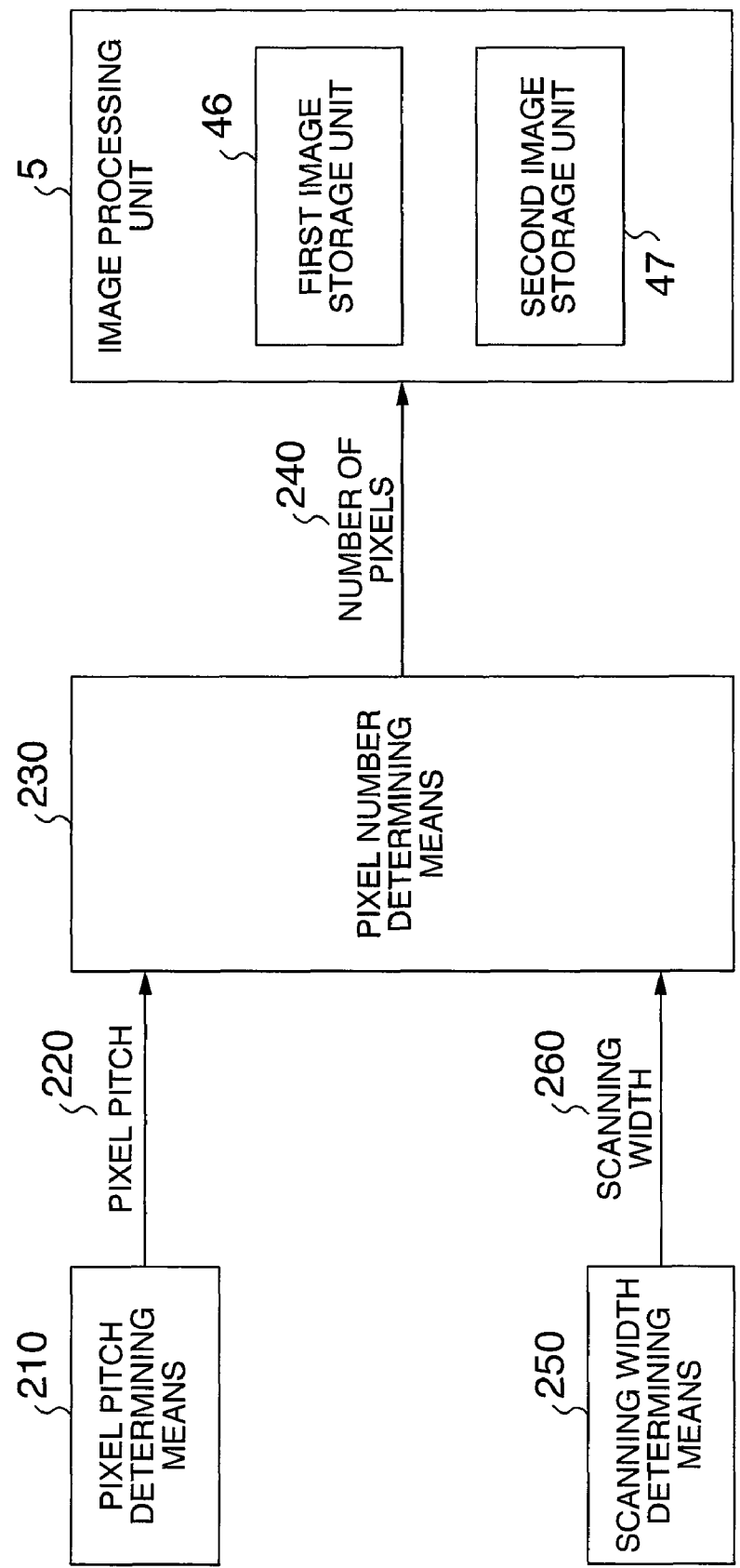

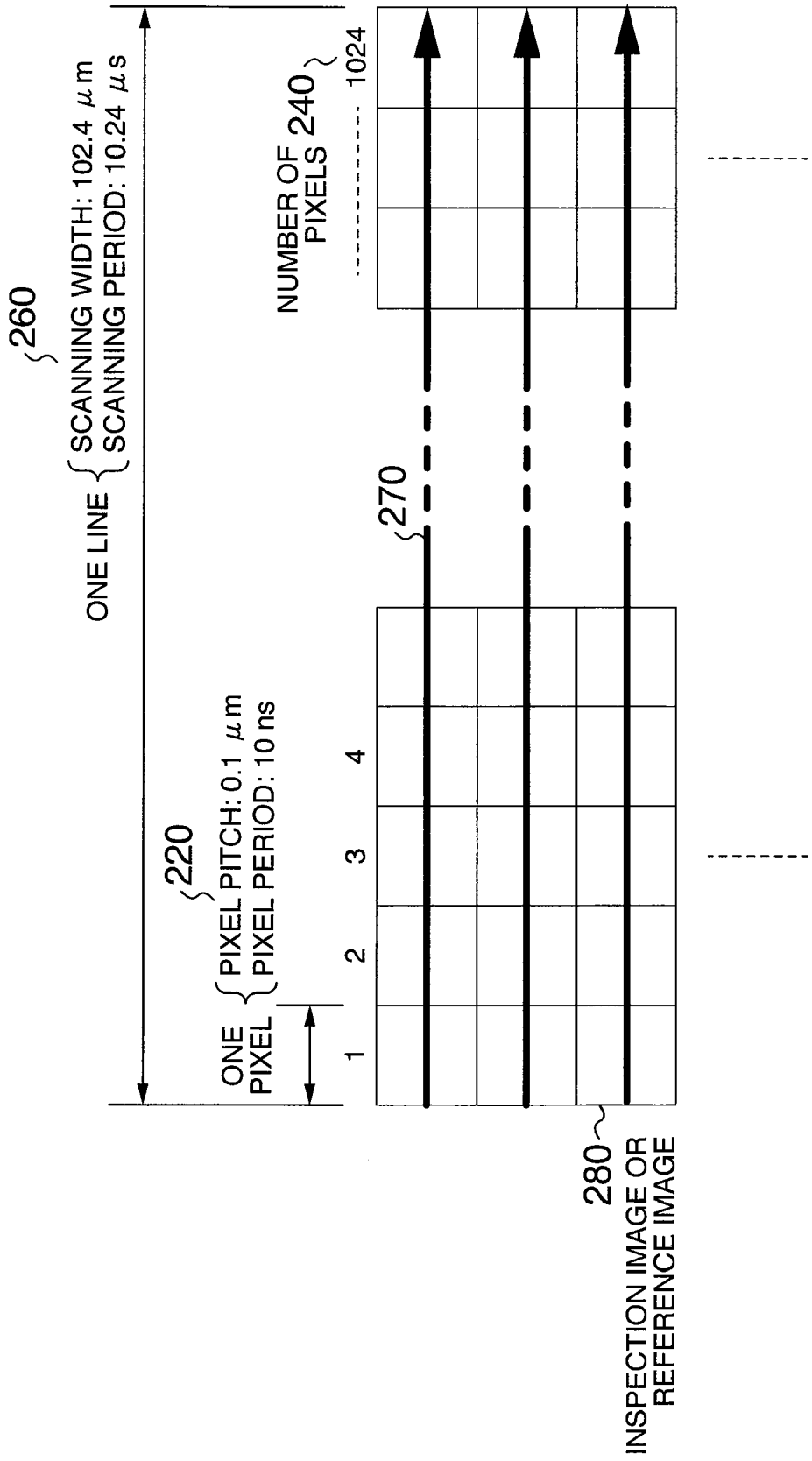

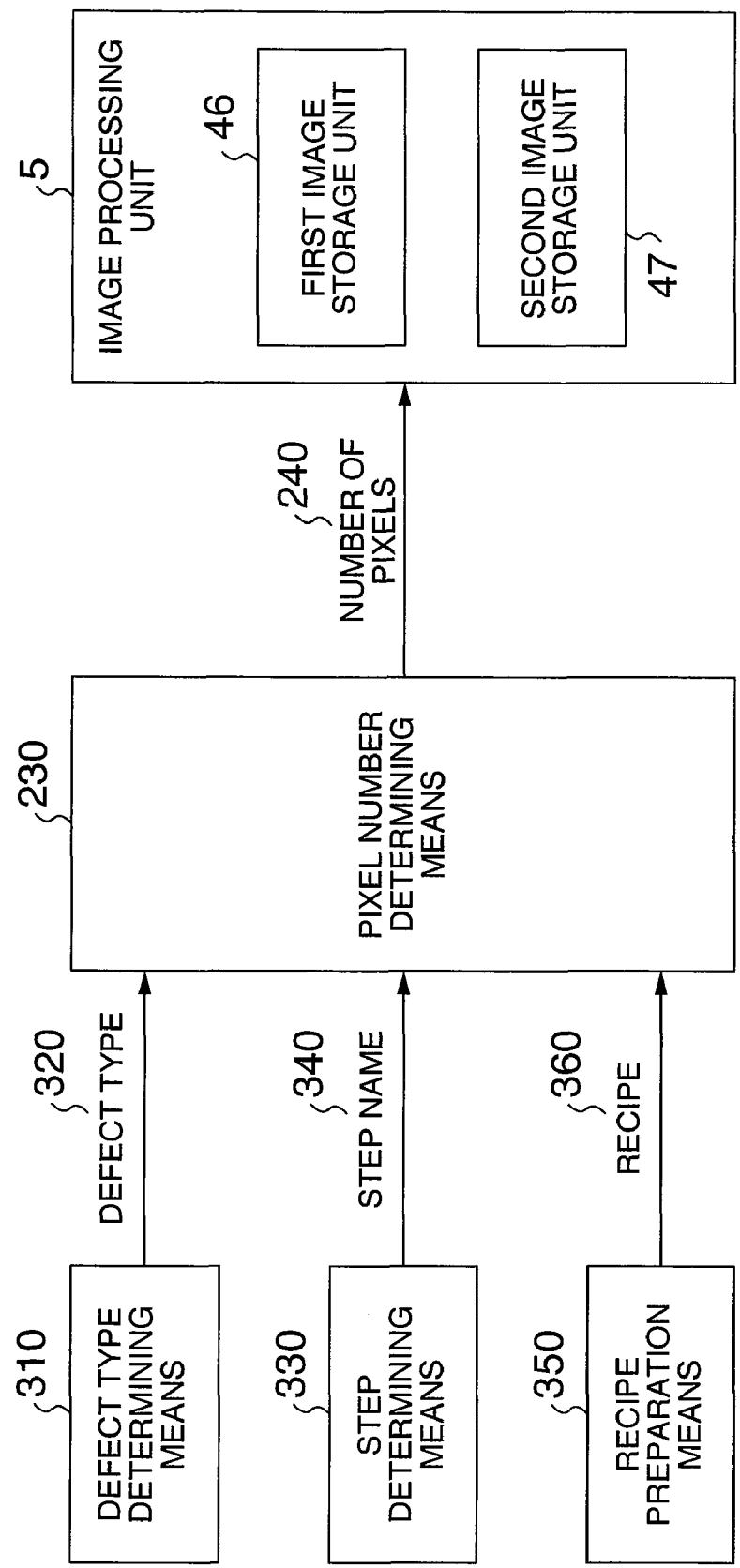

INSPECTION APPARATUS AND INSPECTION METHOD USING ELECTRON BEAM

RELATED APPLICATIONS

This application is a Divisional of U.S. application Ser. No. 11/379,463, filed Apr. 20, 2006, now U.S. Pat. No. 7,518,383, claiming priority of Japanese Application No. 2005-125859, filed Apr. 25, 2005, the entire contents of each of which are hereby incorporated by reference.

BACKGROUND OF THE INVENTION

This invention relates to an inspection apparatus and inspection method using an electron beam for inspecting a semiconductor device, a substrate, a photomask (exposure mask), a liquid crystal, etc. having a fine pattern The semiconductor devices such as the memory and the microcomputer used for the computer are fabricated by repeating the steps of exposure, lithography, etching, etc. on a pattern such as a circuit formed on a photomask. In the fabrication process of the semiconductor device, the success or failure of the result of the steps such as lithography and etching and the presence of a defect such as foreign matter have a great effect on the production yield of the semiconductor device. In order to detect abnormalities or defects at an early time or in advance, the pattern on the semiconductor wafer is inspected at the end of each fabrication step.

According as the diameter of the wafer increases and the circuit pattern is micronized, an image of a high SN ratio is required to be acquired very rapidly to conduct an inspection with a high throughput and a high accuracy. For this purpose, the number of electrons radiated and a high SN ratio are secured by using a large current beam not less than 1000 times (not less than 100 nA) that for the normal scanning electron microscope (SEM). Further, it is essential to detect the secondary electrons and the reflected electrons from the substrate at high speed and with high efficiency.

Also, in order to keep the semiconductor substrate having an insulating film such as a resist free from the effect of the charge, a low-acceleration electron beam of not more than 2 keV is radiated. This technique is described in "ELECTRON • BEAM HANDBOOK" edited by 132 Committee of Japan Society for the Promotion of Science (Nikkan Kogyo Shimbun, Ltd., 1986), Pages 622-623. An electron beam with a large current and a low acceleration, however, causes the aberration due to the space-charge effect and makes the observation with high resolution difficult.

For solving this problem, a method is known in which the high-acceleration electron beam is decelerated immediately before a sample and radiated on the sample as a substantially low-acceleration electron beam. This technique is described, for example, in JP-A-2-142045 and JP-A-6-139985.

JP-A-2003-83917, on the other hand, describes an appearance inspection apparatus using an electron beam, comprising a pixel pitch determining means for determining the pixel pitch along the direction in which pixels making up an image are scanned by the electron beam or a line pitch determining means for determining the line pitch, i.e. the pixel pitch along the direction in which the electron beam is fed, wherein the inspection rate is determined by an inspection rate determining means based on the pixel pitch or the line pitch determined by the pixel pitch determining means or the line pitch determining means, respectively.

The inspection apparatus using the SEM without any optical system poses the problem described below.

In the inspection apparatus of SEM type, the electron beam is scanned on each line in one stroke, and therefore, the throughput is reduced as compared with the optical inspection apparatus which can cover the whole line at a time. This tends to become more conspicuous with the reduction in defect size due to the micronization of the device design rule. This tendency poses another problem even with a defect large in size.

In the case where a defect is small in size, the detection pixel pitch is required to be reduced in accordance with the defect size and the area capable of being inspected in unit time is reduced for a lower throughput. To prevent this inconvenience, the number of pixels making up each line is increased to compensate for the reduced area.

In the case where a defect is large in size, on the other hand, an increase in detection pixel pitch in accordance with the defect size may excessively increase the scanning width determined by the product of the pixel pitch and the number of pixels for the number of pixels increased as in the aforementioned case of small defect size, and the optoelectronic limit may be exceeded, thereby reducing the quality of the peripheral image. As a result, many imaginary defects occur due to the image distortion along the periphery of the image, resulting in an extremely reduced defect detection performance.

SUMMARY OF THE INVENTION

In view of the points described above, the object of this invention is to provide an inspection apparatus and method in which a defect difficult to detect in an optical image cab be detected with high accuracy using an electron beam image, and the problem of the reduced throughput of the inspection apparatus is minimized, while at the same time realizing a high-accuracy defect detection performance in a wide range of defect size from small to large.

This object can be achieved by a SEM-type appearance inspection apparatus for repeatedly scanning the electron beam on a sample formed with a circuit pattern on the surface thereof, generating an inspection image and a reference image based on the secondary electrons generated from the sample and the reflected electrons, and determining a defective portion from the differential image between the inspection image and the reference image, wherein the number of pixels for the generated image can be changed in the direction of repetitive scanning of the electron beam.

Also, the aforementioned object is achieved by a configuration in which the number of pixels is determined by at least one of the pixel pitch in the direction of repetitive scanning of the electron beam and the scanning width.

Further, the aforementioned object is achieved by a configuration in which the number of pixels is increased for a small pixel pitch or a small scanning width, while the number of pixels is decreased for a large pixel pitch or a large scanning width.

The number of pixels may be determined based on the type of the defect, the sample fabrication steps or a corresponding recipe prepared.

The aforementioned objects can also be achieved by a configuration in which the inspection image or the reference image is configured of an image memory with channels divided to a predetermined length, and the number of pixels can be changed by selectively designating the channels.

Further, the aforementioned objects can be achieved by an inspection apparatus including a means permitting the user to input any one of the pixel pitch, the scanning width, the defect type and the name of the step on the sample, or a means for selecting the recipe prepared in accordance with the aforementioned means, wherein the number of pixels is determined based on the information obtained from the input means or the select means.

According to this invention, there is provided a superior inspection apparatus and method for achieving a defect detection performance with high accuracy and high throughput in a wide defect size range from small to large, wherein a defect difficult to detect with an optical image is detected with high accuracy using an electron beam image, while at the same time minimizing the problematic throughput reduction of the inspection apparatus.

Other objects, features and advantages of the invention will become apparent from the following description of the embodiments of the invention taken in conjunction with the accompanying drawings.

BRIEF DESCRIPTION OF THE DRAWINGS

FIGS. 2A and 2B are a block diagram for explaining a pixel number determining means according to a first embodiment of the invention and a diagram for explaining the terms, respectively.

FIG. 3 is a block diagram for explaining a pixel number determining means according to a second embodiment of the invention.

DESCRIPTION OF THE INVENTION

The best mode for carrying out the invention is explained below with reference to the drawings.

First Embodiment

Figure 1:
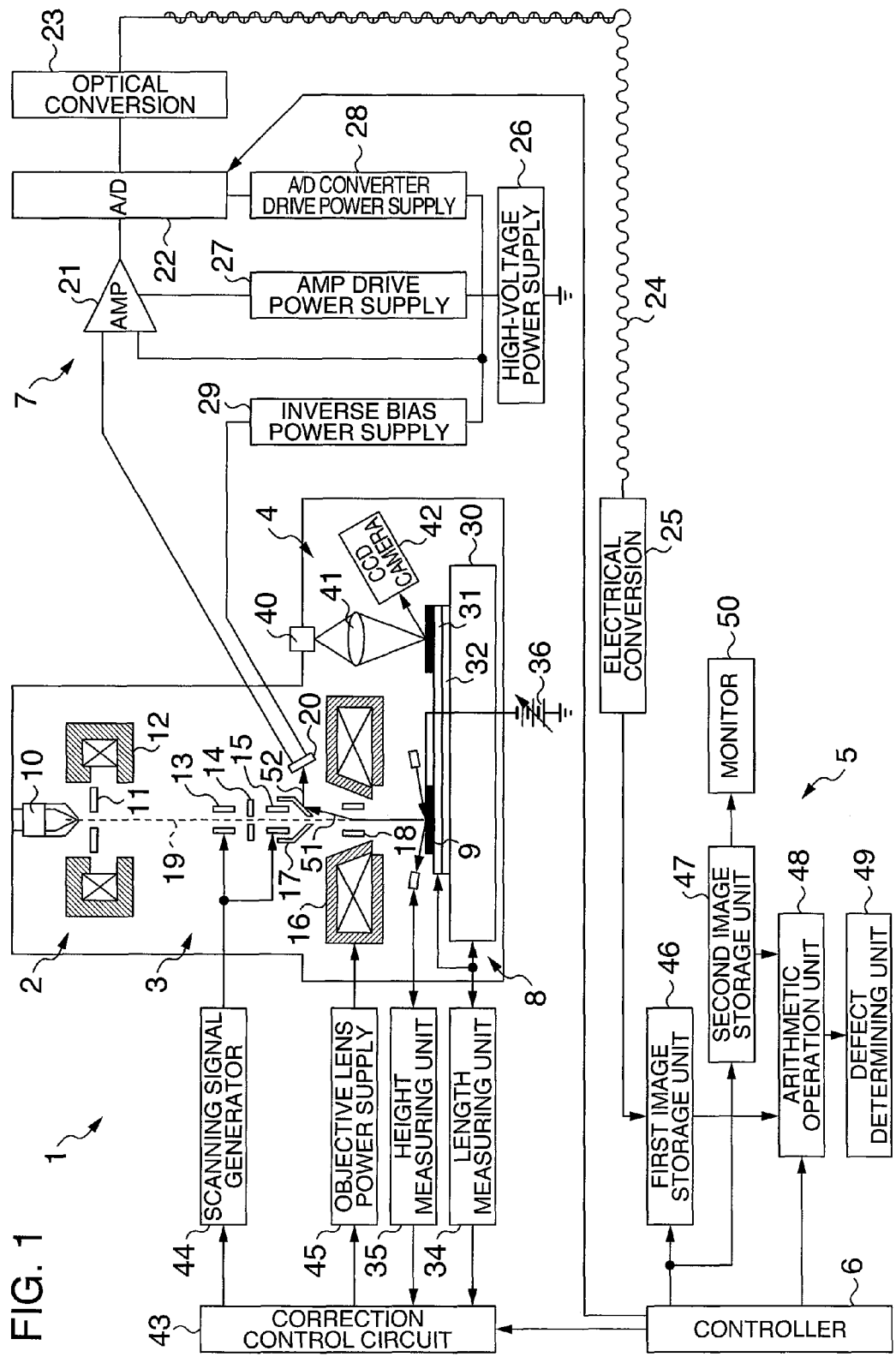
FIG. 1 is a longitudinal sectional view showing a configuration of a SEM-type appearance inspection apparatus.

A first embodiment of the invention is shown in FIGS. 1 to 2B.

FIG. 1 is a longitudinal sectional view showing a configuration of a SEM-type appearance inspection apparatus as an example of the inspection apparatus using a scanning electron microscope according to the invention. The SEM-type appearance inspection apparatus 1 includes an inspection chamber 2 with the interior exhausted into a vacuum state, and a spare room (not shown in this embodiment) for transporting a sample board 9 into the inspection chamber 2. The spare room is adapted to be exhausted into a vacuum independently of the inspection chamber 2. In addition to the inspection chamber 2 and the spare room described above, the SEM-type appearance inspection apparatus 1 includes an image processing unit 5, a controller 6 and a secondary electron detecting unit 7.

The interior of the inspection chamber 2 is roughly configured of an optoelectronic system 3, a sample room 8 and an optical microscope unit 4. The optoelectronic system 3 includes an electron gun 10, a drawing electrode 11 of the electron gun, a condenser lens 12, a blanking deflector 13, a scanning deflector 15, a diaphragm 14, an objective lens 16, a reflecting plate 17 and an ExB deflector 18. A secondary electron detector 20 of the secondary electron detecting unit 7 is arranged above the objective lens 16 in the inspection chamber 2. The output signal of the secondary electron detector 20 is amplified by a preamplifier 21 arranged outside the inspection chamber 2 and converted to a digital data by an A/D converter 22.

The sample room 8 is configured of a sample stage 30, an X stage 31, a Y stage 32, a position monitor length measuring unit 34 and an object inspection board height measuring unit 35. The optical microscope unit 4 is located in the neighborhood of the optoelectronic system 3 in the inspection chamber 2 at an effect-free distance from each other. The distance between the optoelectronic system 3 and the optical microscope unit 4 is thus known. The X stage 31 or the Y stage 32 are adapted to reciprocate over the known distance between the optoelectronic system 3 and the optical microscope unit 4. The optical microscope unit 4 includes a light source 40, an optical lens 41 and a CCD camera 42.

The image processing unit 5 includes a first image storage unit 46, a second image storage unit 47, an arithmetic operation unit 48 and a defect determining unit 49. The electron beam image or the optical image retrieved is displayed on a monitor 50.

The operating instructions and the operating conditions for each unit of the apparatus are input to and output from the controller 6. The controller 6 is supplied in advance with the accelerating voltage for electron beam generation, a deflected width of an electron beam, the deflection rate, the signal drawing timing of the secondary electron detecting unit, the sample stage moving speed and other conditions in a manner capable of being arbitrarily or selectively set for a particular purpose. The controller 6 monitors the displacement of the position and height from the signals of the position monitor length measuring unit 34 and the object inspection board height measuring unit 35 using a correction control circuit 43, and from the monitor result, generates and applies a correction signal to the objective lens power supply 45 and the scanning signal generator 44 in such a manner that the electron beam is always radiated at the right position.

In order to acquire the image of the board 9 to be inspected (also called the object inspection board 9 herein), a reduced thin electron beam 19 is radiated on the object inspection board 9 to generate secondary electrons 51, which are detected in synchronism with the scanning of the electron beam 19 and the movement of the X stage 31 and the Y stage 32. In this way, the image of the object inspection board 9 is obtained.

A high inspection rate is essential for the SEM-type appearance inspection apparatus. Unlike in the conventional ordinary SEM, therefore, the electron beam of an electron beam current on the order of pA is not scanned at low speed, nor a multiplicity of scanning carried out and images are not superposed. Also, at least to suppress the charging of the insulating material, the electron beam is scanned only once or several times at high rate, and not a multiplicity of times. According to this embodiment, therefore, an electron beam of a large current of, say, 100 nA or not less than about 1000 times larger than in the conventional SEM is scanned only once to form an image.

The electron gun 10 uses a thermal field release electron source of diffusion supplement type. By using this electron gun 10, a stable electron beam current can be secured as compared with the conventional tungsten filament electron beam source or the electron source of cold field release type. As a result, an electron beam image with little brightness variations is obtained. Also, a large electron beam current can be set by this electron gun 10, and therefore a high-speed inspection can be realized as described later. The electron beam 19 is drawn from the electron gun 10 by applying a voltage between the electron gun 10 and the drawing electrode 11.

The electron beam 19 is accelerated by applying a high negative potential to the electron gun 10. As a result, the electron beam 19 proceeds toward the sample stage 30 with the energy corresponding to the particular potential, and after being converged by the condenser lens 12, reduced by the objective lens 16 and radiated on the object inspection board 9 mounted on the X stage 31 and the Y stage 32 on the sample stage 30. The object inspection board 9 has a micro circuit pattern such as a semiconductor wafer, a chip, liquid crystal or a mask. The blanking deflector 13 is connected with a scanning signal generator 44 for generating a scanning signal and a blanking signal, and the objective lens 16 is connected with an objective lens power supply 45.

The object inspection board 9 is adapted to be impressed with a negative voltage from a high-voltage power supply 36. By adjusting the voltage of the high-voltage power supply 36, the electron beam 19 can be decelerated and the electron beam radiation energy to the object inspection board 9 can be adjusted to an appropriate value without changing the potential of the electron gun 10.

The secondary electrons 51 generated by radiation of the electron beam 19 on the object inspection board 9 are accelerated by the negative voltage applied to the object inspection board 9. An ExB deflector 18 for curving the track of the secondary electrons without affecting the track of the electron beam 19 by both electric and magnetic fields is arranged above the object inspection board 9 thereby to deflect the accelerated secondary electrons 51 in a predetermined direction. The amount of this deflection can be adjusted by the strength of the electric and magnetic fields applied to the ExB deflector 18. Also, the electric and magnetic fields can be changed in operatively interlocked relation with the negative voltage applied to the object inspection board 9.

The secondary electrons 51 deflected by the ExB deflector 18 impinge on the reflecting plate 17 under predetermined conditions. The reflecting plate 17 is conical and also has the function as a shield pipe to shield the electron beam 19 radiated on the object inspection board 9. With the impingement of the accelerated secondary electrons 51 on the reflecting plate 17, second secondary electrons 52 having the energy of several to 50 eV are generated from the reflecting plate 17.

The secondary electron detecting unit 7 includes a secondary electron detector 20 in the vacuumized inspection chamber 2. The preamplifier 21, the A/D converter 22, an optical conversion means 23, an optical transmission means 24, an electrical conversion means 25, a high voltage power supply 26, a preamplifier drive power supply 27, an A/D converter drive power supply 28 and an inverse bias power supply 29 are arranged outside of the inspection chamber 2. These component parts make up the secondary electron detecting unit 7.

The secondary electron detector 20 of the secondary electron detecting unit 7 is arranged above the objective lens 16 in the inspection chamber 2. The secondary electron detector 20, the preamplifier 21, the A/D converter 22, the optical conversion means 23, the preamplifier drive power supply 27 and the A/D converter drive power supply 28 are floated at the positive potential by the high voltage power supply 26. The secondary electrons generated by impinging on the reflecting plate 17 are introduced to the secondary electron detector 20 by the attraction electric field created by the positive potential.

The secondary electron detector 20 is configured so that the second secondary electrons 52 generated by impingement of the secondary electrons 51 on the reflecting plate 17 are detected in timing with the scanning of the electron beam 19. The output signal of the secondary electron detector 20 is amplified by the preamplifier 21 arranged outside the inspection chamber 2 and converted into a digital data by the A/D converter 22.

The A/D converter 22 is configured so that the analog signal detected by the secondary electron detector 20 is amplified by the preamplifier 21 and, after being immediately converted into a digital signal, transmitted to the image processing unit 5. Since the analog signal detected is digitized and transmitted immediately after detection, a signal higher in SN ratio than in the prior art can be produced at higher rate.

An object inspection board 9 is mounted on the X stage 31 and the Y stage 32. The inspection can be carried out by a method in which the X stage 31 and the Y stage 32 are kept stationary while the electron beam 19 is scanned two-dimensionally or by a method in which the X stage 31 and the Y stage 32 are moved at a predetermined rate in Y direction while the electron beam 19 is scanned linearly in X direction. In the case where a comparatively small specific area is inspected, the former method in which the object inspection board 9 is kept stationary is selected, while the method in which the object inspection board 9 is continuously moved at a predetermined rate is employed for inspecting a comparatively wide area. In the case where the electron beam 19 is required to be blanked, the electron beam 19 can be controlled not to pass through the diaphragm 14 by being deflected by the blanking deflector 13.

As a position monitor length measuring unit 34 for monitoring the position of the X stage 31 and the Y stage 32, a length measuring gauge by laser interference is used in this embodiment. The positions of the X stage 31 and the Y stage 32 can be monitored in real time, and the result thereof is transferred to the control unit 6. Also, the data such as the motor speeds of the X stage 31 and the Y stage 32 are also transferred to the control unit 6 from each driver. Based on these data, the controller 6 can accurately grasp the area and the position irradiated with the electron beam 19. As required, therefore, the displacement of the radiation position of the electron beam 19 can be corrected in real time by the correction controller 43. Also, the area irradiated with the electron beam 19 can be stored for each object inspection board 9.

The object inspection board height measuring unit 35 is an optical measuring unit such as a laser interference measuring unit or a measuring unit of reflected light type for measuring the change from the position of the reflected light, whereby the height of the object inspection board 9 mounted on the X stage 31 and the Y stage 32 can be measured in real time. According to this embodiment, the thin and long white light passed through a slit is radiated on the object inspection board 9 through a transparent window, and the position of the reflected light is detected by a position detection monitor thereby to calculate the amount of change in height from the position change. Based on the measurement data obtained by this optical height measuring unit 35, the focal length of the objective lens 16 is dynamically corrected so that the electron beam 19 is radiated always at the correct focal point on the object inspection board. Also, the warping or height irregularities of the object inspection board 9 may be measured before the electron beam radiation, and the resulting data may be used to set the conditions for correcting each object inspection area of the objective lens 16.

The image processing unit 5 is configured of a first image storage unit 46, a second image storage unit 47, an arithmetic operation unit 48, a defect determining unit 49 and a monitor 50. The image signal of the object inspection board 9 detected by the secondary electron detector 20 is amplified by the preamplifier 21, and after being digitized by the A/D converter 22, converted into an optical signal by the optical conversion means 23 and transferred by the optical transmission means 24. This optical signal, after being converted into an electrical signal again by the electrical conversion means 25, is stored in the first image storage unit 46 or the second image storage unit 47. The arithmetic operation unit 48 carries out the various signal processing operations including the setting the relative positions between, the standardization of the signal level of and the removal of noises from the image signals stored in the first image storage unit 46 and the second image storage unit 47, and compares them with each other. In the defect determining unit 49, the absolute value of the differential image signal produced by the comparison from the arithmetic operation unit 48 is compared with a predetermined threshold value, and in the case where the differential image signal is larger in level than the predetermined threshold value, the particular pixel is determined as a defect candidate, and the position and the number of defects are displayed on the monitor 50.

The general configuration of the SEM-type appearance inspection apparatus is described above. Now, embodiments of the invention are described below.

FIGS. 2A, 2B show a first embodiment of the invention. An inspection apparatus 1 according to the invention includes a controller 6 having a means 230 for determining the number of pixels 240. FIG. 2A is a block diagram showing the operation in which the number of pixels 240 is determined by the pixel pitch 220 and the scanning width 260 and the number of the pixels 240 thus determined is sent to the first image storage unit 46 and the second image storage unit 47 of the image processing unit 5. FIG. 2B is a diagram for explaining the definition of each term.

FIG. 2B schematically shows that an inspection image or a reference image 280 (corresponding to the image generated by the first image storage unit 46 or the second image storage unit 47, respectively, in FIG. 1) is generated by the electron beam scanning 270. The inspection image or the reference image 280 is generated at the rate of one pixel for each period (100 MHz, 10 ns in FIG. 2B) in which the secondary electrons or the reflected electrons generated by the electron beam radiation are detected. The pixel pitch 220 is the length of a particular one pixel along the scanning direction, and one line is formed by scanning the corresponding number of pixels 240 (1024 pixels in FIG. 2B). Also, the length of one line, i.e. the length indicated by the product of the pixel pitch and the number of pixels represents the scanning width 260. By repeating the scanning of each line in this way, the inspection image or the reference image 280 shown is generated.

The pixel number determining means 230 shown in FIG. 2A outputs a large number of pixels and can increase the inspection area correspondingly in the case where the pixel pitch 220 determined by the pixel pitch determining means 210 is small in the selectable range of the pixel pitch, i.e. in the case where a small defect is inspected, thereby preventing the reduction in throughput. In the case where the pixel pitch 220 is large in the selectable pixel pitch range, i.e. in the case where a large defect is inspected, on the other hand, a small number of pixels is output so that the scanning width 260 indicated by the product of the pixel pitch and the number of pixels can be limited. In this way, the deterioration of the image quality in the marginal scanning area is prevented.

With regard to the size of the pixel pitch, a threshold of, say, 0.5 μm may be set to define such a relation that the number of pixels is 2048 (large number of pixels) for the pixel pitch of not more than 0.5 μm (small pixel pitch) and the number of pixels is 1024 (small number of pixels) for the pixel pitch of larger than 0.5 μm (large pixel pitch).

This idea for the pixel pitch 220 also holds true with the scanning width 260 indicating the length in the same direction.

With the configuration shown in FIG. 2A as described above, the throughput and the inspection performance can be improved over a wide range of defect size from small to large.

Second Embodiment

FIG. 3 shows a second embodiment of the invention. The same component elements as those in the first embodiment are designated by the same reference numerals, respectively, as in the first embodiment, and not repeatedly explained as the explanation about the first embodiment applies. As in FIG. 2, the number of pixels 240 may be determined not based on the pixel pitch but based on the defect type, wafer fabrication steps or the corresponding recipe prepared. According to this invention, these factors basically work the same way as the pixel pitch in the first embodiment. Nevertheless, the operating convenience can be improved for the user by determining the number of pixels based on the appropriate factor easier to understand.

The pixel pitch is varied depending on the type of the defect involved (mainly, the defect size and pattern rule). A small defect may be unable to be detected unless inspected at a small pixel pitch. Thus, the defect type can be used instead of the pixel pitch.

Also, the defect type closely depends on the wafer fabrication steps, and the name of a step may be used in place of the pixel pitch.

As another alternative, a recipe incorporating the information such as the pixel pitch, defect type and name of steps can be used with equal effect.

Third Embodiment

Figure 4:
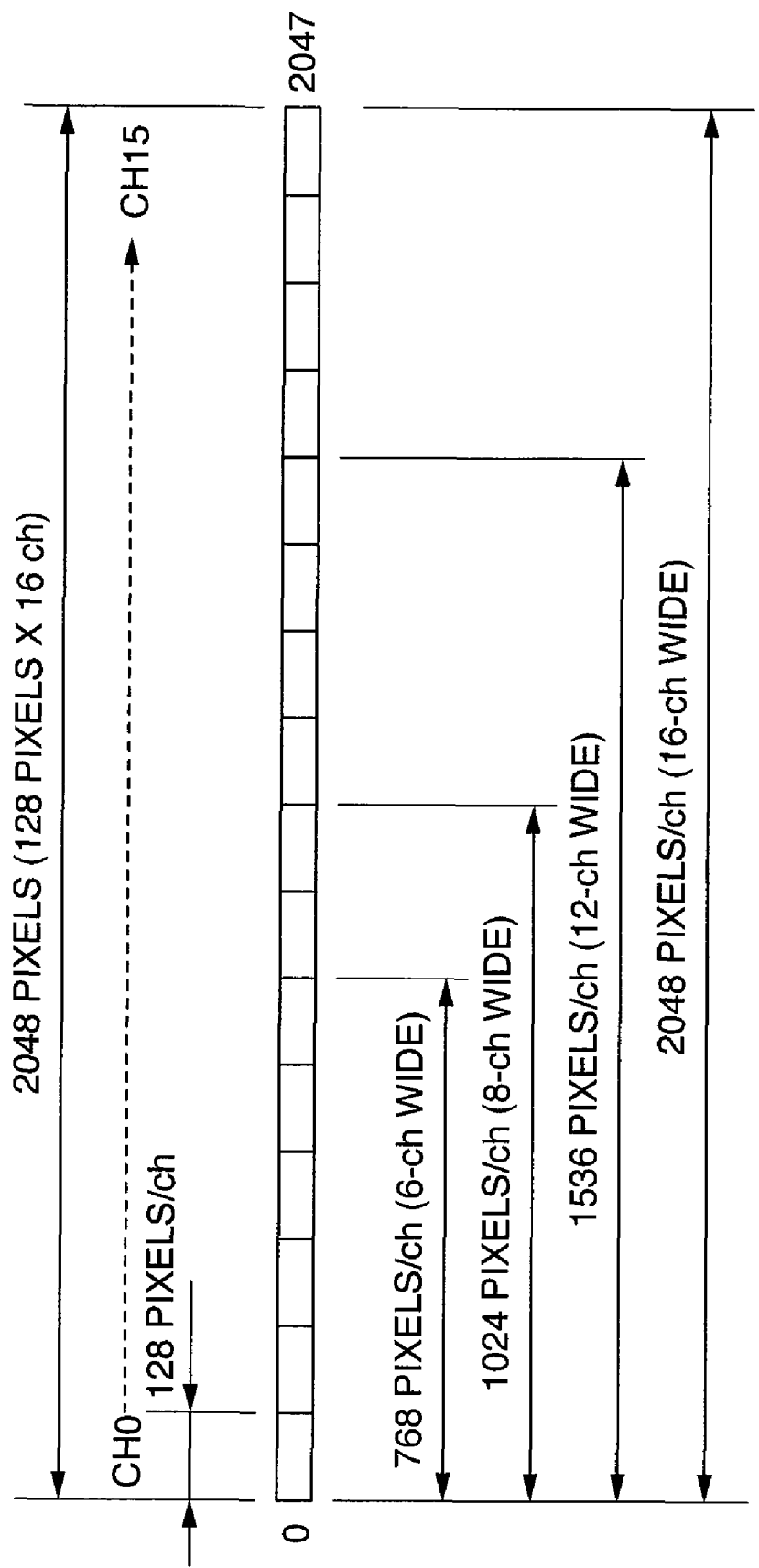
FIG. 4 is a diagram for explaining an image processing unit according to a third embodiment of the invention.

A third embodiment of the invention is shown in FIG. 4. The embodiment of the invention shown in FIG. 4 represents a method in which the number of pixels 240 determined by the pixel number determining means 230 of FIG. 2 is reflected in the inspection image or the reference image 280, i.e. an example of a configuration of the first image storage unit 46 or the second image storage unit 47.

FIG. 4 shows a line memory for a maximum of 2048 pixels per line, and an example in which the channels are divided at the rate of 128 pixels per channel to meet the requirement of the variable number of pixels. Each channel has a valid flag and an invalid flag, an in the case where the number of pixels is reduced from the maximum 2048, only the channels for the required number of pixels are validated to change the number of pixels in units of 128 pixels. The inspection image or the reference image 280 is configured by repeating this line. More specifically, one line is fixed to 16 channels for image processing. Valid channels are shifted to CH0 side, when the number of channels is reduced. In the case, input image data of gradient=0 is stored in each of the reduced channels on the CH15 side. When the number of channels is reduced, only valid channels for image on the CH0 side are processed for imaging.

With the configuration described above, the number of pixels can be easily changed without changing the hardware configuration.

Fourth Embodiment

Figure 5:
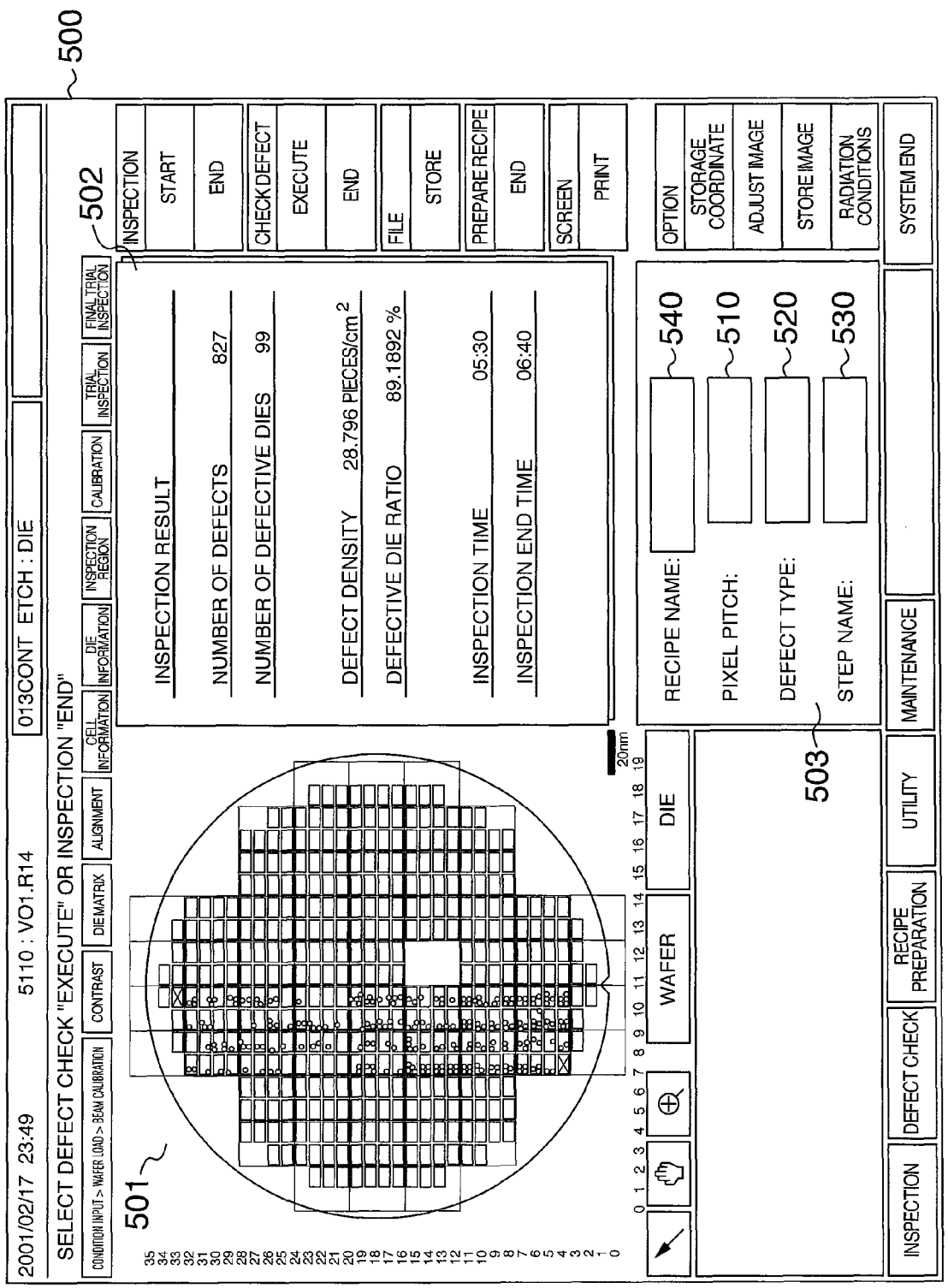
FIG. 5 is a diagram showing an example of monitor display of various input means according to a fourth embodiment of the invention.

FIG. 5 shows a fourth embodiment of the invention. This embodiment represents the input side of the pixel number determining means 230 in FIGS. 2, 3, and an example of the user interface handled by the user (input screen of the monitor 50). As described above, the pixel pitch is the first factor to determine the number of pixels. In the case where the pixel pitch is input by the user, the desired pixel pitch 220 is input to the pixel number determining means 230 through the pixel pitch input means 510, and the number of pixels 240 is output as in the first embodiment. As an alternative, the desired number of pixels may of course be directly input by the user.

In the case where the type of the defect to be inspected can be predicted, the particular type is input to an inspection defect type input means 520, and as in the second embodiment, the number of pixels is determined based on the defect type 320. In this case, the pixel pitch is increased, i.e. the number of pixels is reduced for a comparatively large defect in the potential contrast. In the case where the inspection of minuscule foreign matter or a shape defect is desired, in contrast, the pixel pitch is reduced, i.e. the number of pixels is increased.

On the other hand, a step name input means 530 may be used for inputting the name of a wafer fabrication step, and the number of pixels is determined in accordance with the step name 340. The CMP (chemical mechanical polishing) step for cutting a thin film, for example, often develops the defect of minuscule foreign matter, and the optimum inspection conditions can be automatically established by adjusting the pixel pitch and the number of pixels as described above.

Three types of input means 510, 520, 530 are described above and all of them are not required to be included nor the invention is limited to those means. Also, an inspection recipe containing the whole of these information may be designated by the input means 540. In this case, each detailed information is not required to be input and the input error can be reduced.

According to this embodiment, the inspection conditions can be automatically optimized by inputting the defect type or the step name advantageously for an improved operating convenience.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus comprising:
means for using an electron beam for repeatedly scanning an electron beam on a sample with a circuit pattern formed on the surface thereof, and
means for generating an inspection image and a reference image based on selected one of the secondary electrons generated from the sample and the reflected electrons, and determining a defect from the differential image between the inspection image and the reference image,
wherein the number of pixels in the inspection image and the reference image in the direction of repetitive scanning of the electron beam is variable, and
wherein the number of pixels is determined based on selected one of the type of the defect, the name of a sample fabrication step and a corresponding recipe prepared in advance.

2. An inspection apparatus comprising:
means for using an electron beam for repeatedly scanning an electron beam on a sample with a circuit pattern formed on the surface thereof, and
means for generating an inspection image and a reference image based on selected one of the secondary electrons generated from the sample and the reflected electrons, and determining a defect from the differential image between the inspection image and the reference image,
wherein the number of pixels in the inspection image and the reference image in the direction of repetitive scanning of the electron beam is variable, and
wherein selected one of the inspection image and the reference image is configured of an image memory with the channels thereof divided to a predetermined length, and the number of pixels is changed by selectively designating the channels.

3. An inspection apparatus comprising:
means for using an electron beam for repeatedly scanning an electron beam on a sample with a circuit pattern formed on the surface thereof, and
means for generating an inspection image and a reference image based on selected one of the secondary electrons generated from the sample and the reflected electrons, and determining a defect from the differential image between the inspection image and the reference image,
wherein the number of pixels in the inspection image and the reference image in the direction of repetitive scanning of the electron beam is variable,
wherein the apparatus further comprises one of a means operated by the user to input selected one of the pixel pitch, the scanning width, the defect type and the name of a sample fabrication step and a means for selecting a corresponding recipe prepared in advance, and
wherein the number of pixels is determined based on the information obtained by selected one of the input means and the means for selecting.

4. An inspection method using an electron beam comprising the steps of:
repeatedly scanning an electron beam on a sample with a circuit pattern formed on the surface thereof;
generating an inspection image and a reference image based on selected one of the secondary electrons generated from the sample and the reflected electrons; and
determining a defect from the differential image between the inspection image and the reference image,
wherein the number of pixels in the inspection image and the reference image in the direction of repetitive scanning of the electron beam is variable,
wherein the number of pixels is determined based on selected one of the detect type, the name of a sample fabrication step and a corresponding recipe prepared in advance.

5. An inspection method using an electron beam comprising the steps of:
repeatedly scanning an electron beam on a sample with a circuit pattern formed on the surface thereof;
generating an inspection image and a reference image based on selected one of the secondary electrons generated from the sample and the reflected electrons; and
determining a defect from the differential image between the inspection image and the reference image,
wherein the number of pixels in the inspection image and the reference image in the direction of repetitive scanning of the electron beam is variable,
wherein selected one of the inspection image and the reference image is configured of an image memory with the channels thereof divided to a predetermined length, and the number of pixels can be changed by selectively designating the channels.

6. An inspection method using an electron beam comprising the steps of:

repeatedly scanning an electron beam on a sample with a circuit pattern formed on the surface thereof;

generating an inspection image and a reference image based on selected one of the secondary electrons generated from the sample and the reflected electrons; and determining a defect from the differential image between the inspection image and the reference image, wherein the number of pixels in the inspection image and the reference image in the direction of repetitive scanning of the electron beam is variable, wherein the number of pixels is determined based on the information from selected one of a means operated by the user to input selected one of the pixel pitch, the scanning width, the defect type and the name of a sample fabrication step and a means for selecting a corresponding recipe prepared in advance.

* * * * *